(12) United States Patent
Zenge

(10) Patent No.: US 11,304,619 B2
(45) Date of Patent: Apr. 19, 2022

(54) GENERATING SETTING PARAMETERS FOR AN MRI SEQUENCE

(71) Applicant: Siemens Healthcare GmbH, Erlangen (DE)

(72) Inventor: Michael Zenge, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 235 days.

(21) Appl. No.: 16/515,173

(22) Filed: Jul. 18, 2019

(65) Prior Publication Data

US 2020/0022610 A1 Jan. 23, 2020

(30) Foreign Application Priority Data

Jul. 18, 2018 (EP) .................................... 18184274

(51) Int. Cl.
*A61B 5/055* (2006.01)
*G01R 33/50* (2006.01)
*G06N 3/02* (2006.01)
*G01R 33/54* (2006.01)
*G06N 3/04* (2006.01)
*G06N 3/08* (2006.01)
(Continued)

(52) U.S. Cl.
CPC ............ *A61B 5/055* (2013.01); *A61B 5/7267* (2013.01); *A61B 5/7271* (2013.01); *G01R 33/50* (2013.01); *G06N 3/02* (2013.01); *G06N 3/0454* (2013.01); *G06N 3/084* (2013.01); *G16H 30/00* (2018.01); *G16H 40/63* (2018.01); *G01R 33/543* (2013.01); *G06N 3/0472* (2013.01)

(58) Field of Classification Search
CPC ..... A61B 5/055; A61B 5/7276; A61B 5/7271; G01R 33/50; G01R 33/543; G06N 3/02; G06N 3/084; G06N 3/0472; G06N 3/0454; G16H 40/63; G16H 30/00
USPC ................................................... 324/509–523
See application file for complete search history.

(56) References Cited

U.S. PATENT DOCUMENTS 10,636,141 B2 * 4/2020 Zhou ........................ G06K 9/66
2002/0087066 A1 7/2002 Hellinger
(Continued)

FOREIGN PATENT DOCUMENTS

DE 10055417 A1 5/2002
EP 3282271 A1 2/2018

OTHER PUBLICATIONS

Makhzani, Alireza; Shlens, Jonathon; Jaitly, Navdeep; Goodfellow, Ian; Frey, Brendan: Adversarial Autoencoders. Nov. 17, 2015 (Year: 2015).*

(Continued)

*Primary Examiner* — Judy Nguyen
*Assistant Examiner* — Joseph O Nyamogo
(74) *Attorney, Agent, or Firm* — Schiff Hardin LLP

(57) ABSTRACT

Techniques are described for generating setting parameters for an MRI sequence to be performed, wherein a conditional generative artificial neural network is used that has been trained as part of a conditional generative adversarial net. The techniques also include establishing a conditional generative artificial neural network. The conditioning of the conditional generative artificial neural network can be used to specify a specific medical application or question to obtain setting parameters for an MRI apparatus that are optimized with respect to said application or question.

19 Claims, 2 Drawing Sheets

(51) Int. Cl.
*G16H 40/63* (2018.01)
*A61B 5/00* (2006.01)
*G16H 30/00* (2018.01)

(56) References Cited

U.S. PATENT DOCUMENTS

| | | | |
|---|---|---|---|
| 2008/0091099 A1* | 4/2008 | Carasso | G01R 33/56 600/410 |
| 2017/0007148 A1* | 1/2017 | Kaditz | A61B 5/055 |
| 2018/0038930 A1 | 2/2018 | Kroell | |
| 2020/0020098 A1* | 1/2020 | Odry | G06K 9/6245 |

OTHER PUBLICATIONS

Ian J. Goodfellow, Jean Pouget-Abadie, Mehdi Mirza, Bing Xu, David Warde-Farley, Sherjil Ozairy, Aaron Courville, Yoshua Bengio: Generative Adversarial Nets: Jun. 10, 2014 (Year: 2014).*

Goodfellow, Ian J. et al. "Generative Adversarial Nets" NIPS'14 Proceedings of the 27th International Conference on Neural Information Processing Systems—vol. 2, pp. 2672-2680, Montreal, Canada—Dec. 8-13, 2014 (arXiv:1406.2661v1).

Mirza, Mehdi et al. "Conditional Generative Adversarial Nets" arXiv:1411.1784 [cs.LG], submitted on Nov. 6, 2014, // https://arxiv.org/abs/1411.1784.

Brown, Robert W. et al. "Magnetic Resonance Imaging: Physical Principles and Sequence Design" (2nd Edition) Wiley-Blackwell, May 2014 // ISBN: 978-1-118-63397-7.

Mao, Xudong et al. "Least Squares Generative Adversarial Networks" 2017 IEEE International Conference on Computer Vision (ICCV), Oct. 2017 // DOI: 10.1109/ICCV.2017.304 // arXiv:1611.04076 [cs.CV].

Kristiadi, Augustinus "Generative Adversarial Nets in TensorFlow" Agustinus Kristiadi's Blog, Stand: Dec. 6. 2019 https://wiseodd.github.io/techblog/2016/09/17/gan-tensorflow/.

Kristiadi, Agustinus "Conditional Generative Adversarial Nets in TensorFlow" Agustinus Kristiadi's Blog, Stand: Dec. 6, 2019 https://wiseodd.github.io/techblog/2016/12/24/conditional-gan-tensorflow/.

Elster, Allen D. "An Index System for Comparative Parameter Weighting in MR Imaging" Journal of Computer Assisted Tomography, Vo. 12, No. 1, Jan.-Feb. 1988.

Hornik, Kurt "Multilayer Feedforward Networks are Universal Approximators" Neural Networks, vol. 2, pp. 359-366, 1989.

European Search Report dated Jan. 29, 2019, for Application No. 18184274.1.

* cited by examiner

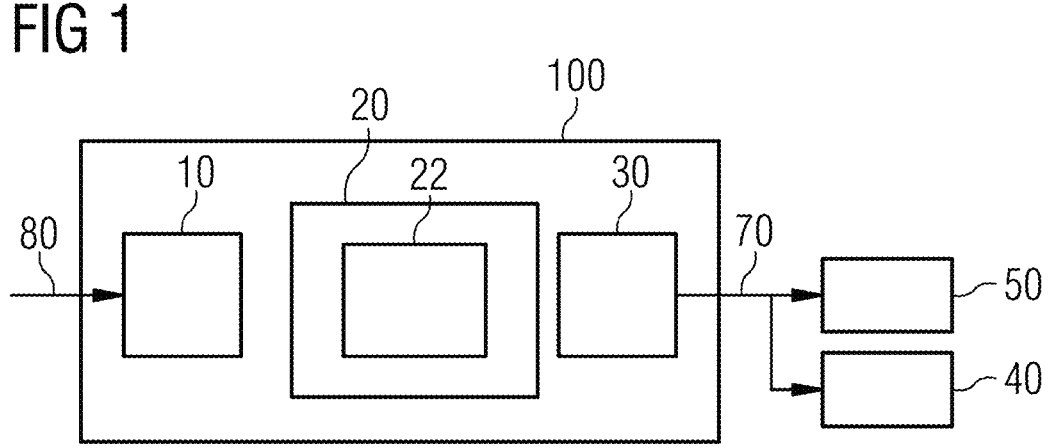
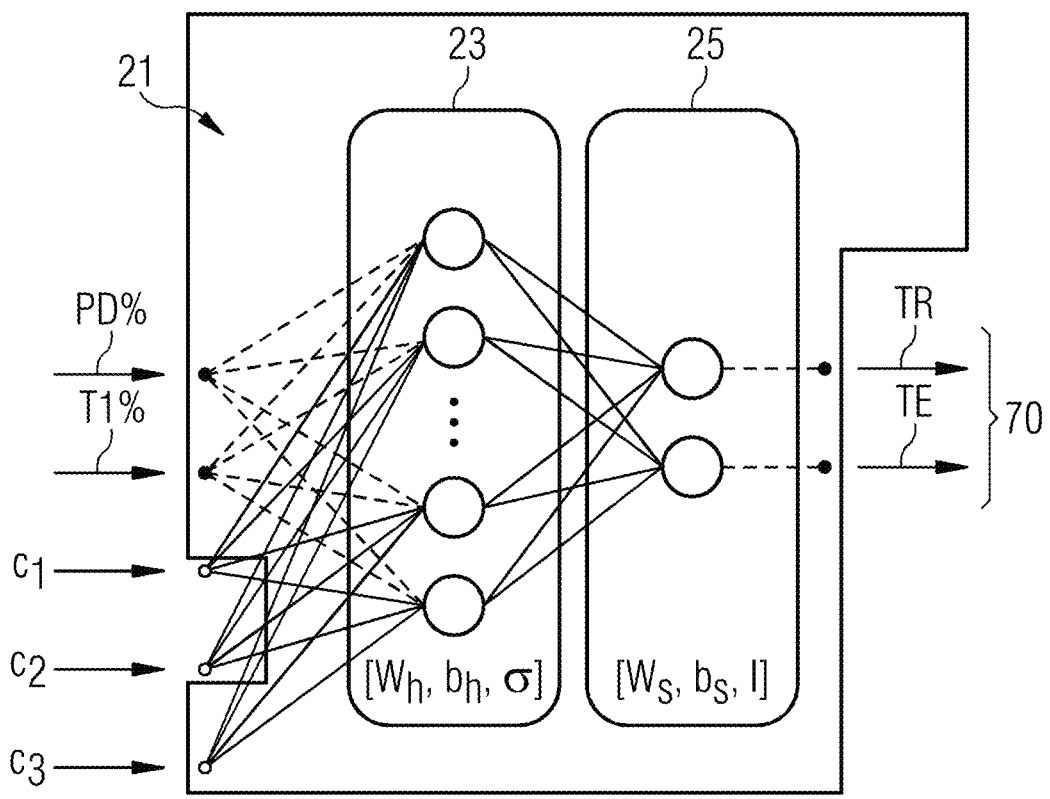

GENERATING SETTING PARAMETERS FOR AN MRI SEQUENCE

CROSS-REFERENCE TO RELATED APPLICATIONS

The present application claims the benefit of the filing date of European patent application no. EP 18184274.1, filed on Jul. 18, 2018, the contents of which are incorporated herein by reference in their entirety.

TECHNICAL FIELD

The present disclosure relates to magnetic resonance imaging (MRI) and, in particular, to techniques for generating setting parameters for an MRI sequence to be performed.

BACKGROUND

Medical imaging plays an important role in the diagnosis and treatment of diseases. One of the best known and established medical imaging procedures is magnetic resonance imaging (MRI). MRI uses setting parameters for an MRI sequence to be performed, and the present techniques to do so still have various drawbacks.

SUMMARY

Magnetic resonance imaging is typically used in radiology in order to form images of the anatomy and/or physiological processes in both healthy and diseased bodies. MRI apparatuses (also called "MRI data acquisition scanners," "MRI scanners," or simply "scanners") use strong magnetic fields, for example stronger than 1 tesla (1 T), electric field gradients, and radio-frequency waves to generate images of body parts.

Magnetic resonance imaging images are usually generated in one or more MRI sequences. An MRI sequence consists of at least one, normally more, radio-frequency pulses ("RF pulses") in accordance with setting parameters of the MRI apparatus.

Put simply, during an MRI procedure, a body is introduced into a static magnetic field generated by a magnet in the MRI apparatus. For this, this body is usually introduced into a tunnel of the MRI apparatus. In response to the strong magnetic field, the spins of the hydrogen nuclei are aligned in the body parallel to the magnetic field, wherein it is optionally possible for additional preliminaries to be performed in order to prepare for the magnetization of the hydrogen nuclei.

After this, the MRI apparatus emits a radio-frequency pulse. If this radio-frequency pulse is emitted at the Larmor frequency it is resonant: phase coherence is created in the precession of the hydrogen nuclei spins. The duration of the radio-frequency pulse is selected such that the spin magnetization of the hydrogen nuclei in the body is aligned perpendicular to the applied magnetic field. In a receiving coil of the MRI apparatus arranged in the vicinity of the body, an electric current is induced by the hydrogen nuclei spins that are still rotating (Larmor precession); this is also called a magnetic resonance signal (MR signal).

The MR signal fades over time due to two relaxation processes. The loss of coherence of the spin system attenuates the MR signal with a time constant, which is usually called the "transverse relaxation time" and designated "T2". At the same time, the magnetization vector gradually relaxes back to its equilibrium alignment parallel to the magnetic field. This takes place with a time constant known as the "spin-lattice relaxation time" or "longitudinal relaxation time" and is designated "T1."

Spatial resolution of the MR signal is generated by the use of a magnetic field gradient (i.e. a gradient of the magnetic field) that causes the hydrogen nuclei spins to precess at different locations (usually in different layers of the body) at a slightly different speed. This can be used in order to localize or trigger signal origins within the body.

The contrast in MRI images is usually due to the fact that different components of the body (in particular bone, tissue, etc.) generally have different relaxation times T1 and T2. Since this is particularly the case with soft tissue types, MRI images usually provide good resolution for such soft tissue. Hence, the selection of optimal MRI sequences (or, in other words, the performance of the MRI process with optimally-selected setting parameters) can maximize the contrast for tissue of interest or of a body part of interest (for example, a specific organ). This can improve the chances of successful diagnosis and treatment.

Generally, a plurality of MRI sequences is required in order to depict tissue adequately. A combination of MRI sequences (frequently together with specific locations and/or alignments or sectional planes) is frequently designated by an MRI protocol. A user of the MRI apparatus (frequently a radiologist) adapts the MRI sequences in order to provide the best possible imaging for a specific medical question.

An MRI sequence is usually described by a plurality of setting parameters comprising, partially as a function of the specific MRI sequence performed, for example: an echo time (TE), a repetition time (TR), a flip angle, a bandwidth of the radio-frequency pulse, a turbo factor (also called pulse-train length), a gradient during the radio-frequency pulse excitation ("spoiling gradient" or "crusher gradient"), etc.

Two decisive setting parameters are the repetition time (usually abbreviated to TR) and the echo time (usually abbreviated to TE), which are normally measured and reported in milliseconds (as, for example, in the code snippets reproduced below).

The echo time, TE, indicates the duration from the center of the radio-frequency pulse to the center of the echo, i.e. of the induced signal. For MRI sequences with a plurality of echoes between each radio-frequency pulse, it is possible for a plurality of echo times to be defined; these are usually designated TE1, TE2, TE3, etc.

The repetition time, TR, is the duration between mutually-corresponding sequential points of a recurrent series of radio-frequency pulses (or echoes).

The most frequently used MRI sequences include the so-called T1-weighted MRI sequence ("T1-weighting"), the so-called T2-weighted MRI sequence ("T2-weighting"), and the proton-density-weighted MRI sequence ("PD-weighting").

With T1-weighting, the repetition time TR is usually short compared to the longest longitudinal relaxation time T1 of the tissue of interest, and the echo time TE is short in relation to the transverse relaxation time T2 of the tissue of interest. This reduces T2 contributions to the image contrast.

In the case of T2-weighting, the repetition time TR is usually long compared to the longitudinal relaxation time T1 of the tissue (in order to reduce T1 contributions), and the echo time TE is selected between the longest and the shortest transverse relaxation time T2 of the tissue of interest.

It is evident that a specific MRI sequence can be T1-weighted for a specific type of tissue and have another type of weighting for another type of tissue.

A proton-density-weighted MRI sequence can be achieved by using a long repetition time TR and a short echo time TE.

For a more detailed discussion of the technical background of MRI methods, reference is made to Brown (see reference [1]).

Specific MRI protocols exist for many diseases and/or body parts. To date, the creation of optimal MRI sequences and MRI protocols has required many years of practice and experience, in particular if contrast has to be optimized for a specific medical question (for example the presence of a tumor).

Since adequately trained staff are not always available, it is desirable to reduce the complexity of the operation of MRI facilities and the user interface of an MRI apparatus.

Known from the field of machine learning and artificial intelligence are generative adversarial nets (GAN), such as one discussed in Goodfellow (see reference [2]).

Goodfellow describes a generative adversarial net in which two networks are trained substantially simultaneously as adversaries: a generative part, i.e. a generative artificial neural network, and a discriminative part, i.e. a discriminative artificial neural network.

The generative artificial neural network is trained to generate its own data distribution based on an original data distribution (training data). The discriminative artificial neural network is trained to identify whether a specific dataset belongs to the original data distribution or to the data distribution generated by the generative artificial neural network. The ideal situation is achieved when the discriminative artificial neural network is no longer able to discriminate between the datasets of the original data distribution and those of the generated data distribution.

One example of generative adversarial nets includes conditional generative adversarial nets, which are specifically described in particular in Mirza (see reference [3]).

In conditional generative adversarial nets, a conditioning element (normally a vector, i.e. a "condition vector") is introduced both with the generative artificial neural network and with the discriminative artificial neural network, as a result of which it is possible to generate (or discriminate between) datasets adapted to different situations or target regions (which are modeled by the conditions). In this context, the setting of such a condition is mainly designated "conditioning," and the "conditionality" of the network means that it is able to observe such conditions and to generate its task under the condition(s) that may have been set.

A further known variant of generative adversarial nets is a least squares generative adversarial net, which is described, for example, in Mao (see reference [4]).

With this in mind, it is an object of the present disclosure to provide improved systems and methods for generating setting parameters for an MRI sequence to be performed by an MRI apparatus. This object is achieved by the embodiments of the present disclosure as further discussed herein.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

FIG. 1 illustrates a schematic block diagram of a system in accordance with an embodiment of the disclosure;

FIG. 2 illustrates a schematic representation of the trained conditional generative artificial neural network of the system in accordance with FIG. 1;

The exemplary embodiments of the present disclosure will be described with reference to the accompanying drawings. The drawing in which an element first appears is typically indicated by the leftmost digit(s) in the corresponding reference number.

Figure 3:
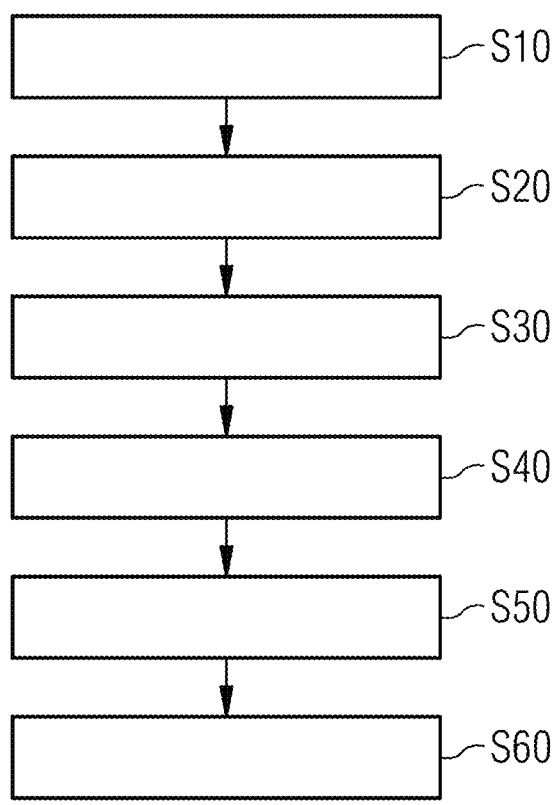
FIG. 3 illustrates a schematic flow diagram to explain a method for establishing a system for generating setting parameters for an MRI sequence to be performed in accordance with an embodiment of the disclosure.

The attached figures are intended to enable a deeper understanding of the embodiments of the invention. They illustrate embodiments and are used in conjunction with the description to clarify principles and concepts of the invention. Other embodiments and many of the aforementioned advantages are apparent in the light of the drawings. The elements of the drawings are not necessarily shown true to scale with respect to one another.

In the figures of the drawing, identical, functionally identical and identically acting elements, features and components are each provided with the same reference characters, unless stated otherwise.

DETAILED DESCRIPTION

In accordance with an embodiment as described further herein, a system is provided for generating setting parameters for a magnetic resonance imaging (MRI) sequence to be performed comprising:

an input interface, which is configured to receive input data relating to the MRI sequence to be performed;

a computing facility, which is embodied to implement a conditional generative artificial neural network, wherein the conditional generative artificial neural network is embodied and trained to generate setting parameters for the MRI sequence to be performed based on the input data received from the input interface;

wherein the conditional generative artificial neural network is conditional in order to generate setting parameters for in each case at least one T1-weighted MRI sequence, one T2-weighted MRI sequence and one proton-density-weighted (PD-weighted) MRI sequence.

The system can be integrated in an MRI apparatus. Accordingly, in accordance with a further embodiment, the disclosure also provides an MRI apparatus comprising the system and further elements, for example a magnetic-field generator (electromagnet), a high-frequency pulse generator, a tunnel, a control facility and the like.

The computing facility can be any apparatus, or any means, for computing, i.e. for executing software, an app or an algorithm. For example, the computing facility can be an individual processing unit, a microprocessor, an application-specific integrated circuit (ASIC) or the like. The computing facility may comprise an arrangement of processing cores, for example central processing cores (CPUs) and/or graphics processing cores (GPUs).

The computing facility can also be partially or completely implemented by interconnected remotely located devices, for example by cloud computing services and/or as a virtual machine. The computing facility can also be integrated in a control facility of an MRI apparatus.

The conditional generative artificial neural network may be implemented as a feedforward network, such as a multilayer perceptron, for instance. This enables particularly simple training of the neural network by means of back-propagation.

The conditional generative artificial neural network may be conditioned (i.e. provided with conditions that are to be fulfilled) in that the original input vectors are concatenated with a corresponding condition vector, wherein the condition vector indicates a type of MRI sequence (for example a T1-weighted MRI sequence, a T2-weighted MRI sequence, a PD-weighted MRI sequence) to which the respective original input vector belongs. As already mentioned in connection with the Mirza reference, the same type of condition vector may be used for both the generative and the discriminative conditioned neural network. This will be also illustrated below in connection with various code examples.

In embodiments, the condition vector c can, for example, be constructed such that it has an entry with a value of "1" at a position $c_i$, which indicates a first type of MRI sequence (for example a T1-weighted MRI sequence, a T2-weighted MRI sequence, a PD-weighted MRI sequence, etc.) and that, at all other positions $c_{j\neq i}$, it has entries with a value of "0," For example, a vector with the structure $(1,0,0)^T$ can indicate a T1-weighted MRI sequence, a vector with the structure $(0,1,0)^T$ a T2-weighted MRI sequence, and a vector with the structure $(0,0,1)^T$ a PD-weighted MRI sequence.

The condition vector can also contain one or more further conditions, for example a condition that indicates a body part to be examined, a body-fat percentage, a desired artifact suppression, or the like.

In accordance with the embodiments described herein, a conditional generative artificial neural network is particularly suitable for the special technical field of the generation of setting parameters for MRI sequences, and can be optimally adapted for this task with a multiplicity of variants and options. Hence, the disclosure enables the generation of optimal setting parameters for MRI sequences based on training data without requiring the participation of a radiologist.

In accordance with an embodiment of the disclosure, a method is provided for establishing a system for generating setting parameters for an MRI sequence to be performed, as described above. Herein, the method comprises at least the steps:

the provision of training data comprising input data relating to the MRI sequence to be performed and comprising corresponding setting parameters as labels;

the provision of a conditional generative artificial neural network and a conditional discriminative artificial neural network;

training the conditional generative artificial neural network using the training data provided, wherein the conditional generative artificial neural network is trained in order to generate the setting parameters for MRI sequences to be performed based on the input data for the training data;

wherein the conditional generative artificial neural network is conditional in order to generate setting parameters for in each case at least one T1-weighted MRI sequence, one T2-weighted MRI sequence and one proton-density-weighted MRI sequence;

training the conditional discriminative artificial neural network using the training data provided and the setting parameters generated by the conditional generative artificial neural network, wherein the conditional discriminative artificial neural network is trained in order to discriminate for each individual parameter set whether this belongs to the training data or to the setting parameters generated by the conditional generative artificial neural network;

and wherein the training of the conditional generative artificial neural network comprises training the conditional generative artificial neural network so as to generate the setting parameters such that the conditional discriminative artificial neural network is not able to discriminate the training data from the setting parameters generated by the conditional generative artificial neural network;

the provision and configuration of an input interface for receiving input data relating to MRI sequences to be performed; and the provision and configuration of a computing facility for implementing the trained conditional generative artificial neural network for generating the setting parameters for the MRI sequence to be performed based on the received input data.

The method embodiment as described herein is suitable for establishing the system embodiment as discussed herein. The method embodiment can advantageously be adapted in accordance with all the variants, modifications, embodiments, and developments described with reference to the system embodiment, and vice versa.

The disclosure further provides in accordance with another embodiment a method for generating setting parameters for an MRI sequence to be performed comprising at least the steps:

receiving input data relating to the MRI sequence to be performed;

generating, using a trained conditional generative artificial neural network, setting parameters for the MRI sequence to be performed based on the received input data;

wherein the conditional generative artificial neural network is conditional in order to generate setting parameters for in each case at least one T1-weighted MRI sequence, one T2-weighted MRI sequence and one proton-density-weighted MRI sequence.

The method in accordance with this embodiment is in particular suitable for performance with the system embodiments described above. The method embodiment can advantageously be adapted in accordance with all the variants, modifications, embodiments, and developments described with reference to the system embodiment, and vice versa.

In accordance with yet another embodiment, a computer program product is described comprising executable program code to perform any of the method embodiments described herein when the executable program code is executed.

In addition, other embodiments provide a volatile or non-volatile data-storage medium comprising executable program code to perform any of the method embodiments described herein when the executable program code is executed. The data-storage medium may be implemented as a non-transitory computer-readable medium such as, for example, a hard disk, a memory stick, a DVD, a Blu-ray disk, etc.

In addition, other embodiments include providing a data stream comprising or representing executable program code to perform any of the method embodiments described herein when the executable program code is executed.

Further advantageous embodiments, variants, and developments may be derived from the subclaims and the description in conjunction with the Figures.

In some embodiments, the input data comprises at least one of the following percentages:
- a percentage with which the MRI sequence to be performed is to be T1-weighted
- a percentage with which the MRI sequence to be performed is to be T2-weighted
- a percentage with which the MRI sequence to be performed is to be proton-density-weighted.

Values for this input data (or: "input parameters") can, for example, be stored in tables for different medical tasks and can accordingly also be input into the system by untrained staff. The system can receive these input parameters and, optionally using further input parameters, generate corresponding setting parameters for an MRI apparatus therefrom.

Advantageously, two of the three percentages named may be used as input data, wherein the corresponding third percentage is obtained from the difference between one hundred and the sum of the two percentages used. In other words, the sum of the three percentages may equal one hundred. This enables large areas of the MRI sequences used in medical applications to be covered with simple means.

Correspondingly, in cases in which the system is designed to generate setting parameters for more than only T1-weighted, T2-weighted and PD-weighted MRI sequences, further percentages can be used as input data for the corresponding weightings, wherein, once again, it can be provided that the sum total of all settable percentages adds up to one hundred.

In some embodiments, the setting parameters comprise a repetition time TR and/or an echo time TE for the MRI sequence to be performed. In other words, with these embodiments, the system is configured to also generate at least a repetition time and/or an echo time of the MRI sequence.

In some embodiments, the setting parameters include the repetition time TR and the echo time TE. In this case, an output layer of the conditional generative artificial neural network can include two output nodes, of which the first outputs a value for the repetition time TR, and the second a value for the echo time TE. In accordance with such embodiments, generating these two setting parameters with optimal values achieves a satisfactory overall result of the MRI sequence.

If the setting parameters generated by the system are expanded in order to generate more setting parameters than the repetition time TR and the echo time TE, this can increase the computational effort required (and thus possibly also the amount of hardware required). On the other hand, this will further improve the quality of the result of the MRI sequences and will be particularly advantageous in the case of particularly difficult (for example, inherently low-contrast) imaging tasks.

In some embodiments, the setting parameters may comprise a turbo factor and/or a bandwidth for the MRI sequence to be performed. The turbo factor (also called the "pulse-train length") designates the number of echoes combined in a series of echo imaging procedures to form a single image or a group of images. Such methods comprise, for example "Rapid Acquisition with Relaxation Enhancement" (RARE), "Fast Spin Echo" (FSE), and "Turbo Spin Echo" (TSE). In accordance with the embodiments as described herein, setting parameters may also be particularly suitable for generation by the system as described in further detail in the present disclosure.

In some embodiments, the conditional generative artificial neural network can be conditioned by a magnetic field strength for the MRI sequence to be performed, i.e., the conditional generative artificial neural network can be trained and configured to generate the setting parameters (if the corresponding condition is set) on condition that a specific magnetic field strength is generated by the MRI apparatus (e.g., for field strength values of 1.5 Tesla and 3 Tesla). Namely, the optimal setting parameters may change as a function of the magnetic field strength that is applied by the MRI apparatus. The system according to the embodiments as described herein is suitable for calculating these changes.

Hence, if the system as further described herein comprises an MRI apparatus or is integrated in an MRI apparatus, this MRI apparatus can advantageously be embodied such that when a user changes a setting for the magnetic field strength, the system automatically generates correspondingly adapted new optimal setting parameters using the conditional generative artificial neural network.

In some embodiments, the conditional generative artificial neural network is additionally conditional due to at least one of the following conditions:
- information regarding a location and/or an alignment of a sectional plane through a body on which the MRI sequence is to be performed,
- information regarding a location and/or a body part of a body on which the MRI sequence is to be performed,
- a body-fat percentage,
- a desired artifact suppression.

Typical sectional-plane alignments are the transverse alignment, the sagittal alignment, and the coronal alignment. This enables the setting parameters generated to be even better adapted to the medical task (for example diagnosis).

Body parts can include any body part suitable for MRI scanning such as, for example, a human knee, a human brain, a human heart, etc. This again enables the setting parameters generated to be even better adapted to the medical task.

In some embodiments, the conditional generative artificial neural network has been trained as part of a conditional generative adversarial net, wherein the conditional generative adversarial net comprises the conditional generative artificial neural network as its generative part and a conditional discriminative artificial neural network as its discriminative part.

With respect to the basic principles of adversarial nets, reference is made again by way of example to Goodfellow and Mirza, wherein the conditional generative artificial neural network of the present invention functions as a "generative model" or a "generative network," and the conditional discriminative artificial neural network functions as a "discriminative model" or a "discriminative network."

It has surprisingly been found that these techniques can be used for the present specific technical application, namely the generation of setting parameters for MRI sequences, with very good results.

In some embodiments, the conditional generative artificial neural network includes an input layer, an output layer, and an individual, intermediate hidden layer. It has been found that this comparatively simple arrangement can be sufficient to satisfy the complex requirements for setting parameters for MRI sequences. The hidden layer may advantageously be comprised of any suitable number of nodes (e.g., more than five nodes, more than ten nodes, more than twenty nodes, more than forty nodes, more than forty-eight nodes, etc.).

In some embodiments, the output layer advantageously includes one node for each setting parameter to be generated. Hence, if only the echo time TE and the repetition time TR are generated, the output layer can advantageously consist of exactly two nodes.

In some embodiments, the conditional generative artificial neural network comprises an input layer, an output layer, and at least one hidden layer (or "latent layer"). The input layer and the at least one hidden layer can form at least part of an autoencoder network. Such networks form a high-dimensional input vector in a (usually) lower-dimensional latent space. Hence, such autoencoders can be used to reduce the computational effort in that less relevant data (or input-vector entries) are eliminated or only taken into account to a small extent in the latent space. Autoencoders can also be used to interpolate missing information in the input vector.

In some embodiments, the training of the conditional generative artificial neural network and/or the training of the conditional discriminative artificial neural network is performed using a loss function based on the least squares method.

The above embodiments and developments can be combined with one another in any meaningful way. Further possible embodiments, developments, and implementations of the disclosure also include non-explicitly named combinations of features as described above, elsewhere herein, with reference to the exemplary embodiments. Herein, the person skilled in the art may also add individual aspects as improvements or additions to the embodiments as described in the present disclosure.

FIG. 1 illustrates a schematic block diagram of a system in accordance with an embodiment of the disclosure. FIG. 1 shows a schematic block diagram of a system 100 in accordance with an embodiment of the present disclosure for generating setting parameters 70 for a magnetic resonance imaging (MRI) sequence to be performed.

As shown in FIG. 1, the system 100 comprises an input interface 10, which is configured to receive input data 80 ("input data") relating to the MRI sequence to be performed.

In the present embodiment, the input data 80 comprises a percentage PD % with which the MRI sequence to be performed is to be PD-weighted, and a second percentage T1% with which the MRI sequence to be performed is to be T1-weighted. The system 100 is furthermore configured such that the MRI sequence to be performed is to be T2-weighted with a third percentage, T2%, wherein the following should apply:

$$T1\% + T2\% + PD\% = 1$$

Accordingly, two of the three percentages T1%, T2%, and PD %, (e.g., PD % and T1%), are sufficient as input data 80 to define the weighting for the MRI sequence to be performed in all three percentages. Hence, for a setting of PD %=100, T1%=0 describes a fully PD-weighted MRI sequence, and for conditions T2%=0, a setting of PD %=50, T1%=25 conditions a setting of T2%=25, and so on.

The system 100 further comprises a computing facility 20, which may be implemented, for instance, as a conditional generative artificial neural network 22.

In the present embodiment, the conditional generative artificial neural network 22 may be embodied and trained to generate the setting parameters 71 for the MRI sequence to be performed based on the input data 80 received from the input interfaces 10. The conditional generative artificial neural network 22 is conditioned such that it is able to generate setting parameters for, in each case, at least one T1-weighted MRI sequence, one T2-weighted MRI sequence, and one proton-density-weighted (PD-weighted) MRI sequence.

The conditional generative artificial neural network 22 can be conditioned (e.g., be provided with conditions that are to be fulfilled) in that the original input vectors thereof (i.e. in the present case, for example, a vector with a first entry that indicates or specifies PD % and with a second entry that indicates or specifies T1%) are concatenated with a corresponding condition vector. The condition vector indicates a type of MRI (e.g., T1-weighted MRI sequence, T2-weighted MRI sequence, PD-weighted MRI sequence) to which the respective original input vector belongs.

The condition vector c can, for example, be constructed such that the condition vector c has an entry with a value of "1" at a position $c_i$, which indicates a first type of MRI sequence (e.g., a T1-weighted MRI sequence, T2-weighted MRI sequence, PD-weighted MRI sequence), and at all other positions $c_{j \neq i}$, it has entries with a value of "0." For example, a vector with the structure $(1,0,0)^T$ can indicate a T1-weighted MRI sequence, a vector with the structure $(0,1,0)^T$ can indicate a T2-weighted MRI sequence, and a vector with the structure $(0,0,1)^T$ can indicate a PD-weighted MRI sequence. Hence, mixed-weighting of, for example, 50% PD-weighted and 50% T1-weighted can be indicated by a condition vector with the structure $(0.5, 0, 0.5)^T$.

The condition vector can also contain one or more further conditions, for example a condition that indicates a body part to be examined, a body-fat percentage, a desired artifact suppression, etc.

As already explained above, it is also possible for further conditions to be set for the conditional generative artificial neural network 22, for example a magnetic field strength for the MRI sequence to be performed. It is namely known that, for example, the repetition time TR and the echo time TE change if, instead of a magnetic field strength of one-and-a-half Tesla (1.5 T), a magnetic field strength of three Tesla (3 T) is set.

The system 100 comprises an output interface 30 via which the generated setting parameters 70 can be output, for example to a display apparatus 40 (e.g., a screen or touchscreen) to display the generated setting parameters 70 and/or the generated setting parameters 70 can be output to an MRI apparatus 50. Although illustrated in FIG. 1 as separate components, embodiments include the display apparatus 40 and/or the MRI apparatus 50 being part of the system 100. The MRI apparatus 50 can be implemented such that it is automatically set by the setting parameters 70 output by the output interface 30.

Accordingly, the present disclosure also provides a method for displaying optimal setting parameters 70 and a method for automatically setting an MRI apparatus 50 with optimal setting parameters 70.

FIG. 2 illustrates a schematic representation of the trained conditional generative artificial neural network of the system in accordance with FIG. 1. FIG. 2 shows a schematic representation of an example structure of the trained conditional generative artificial neural network 22, which may be implemented by the computing facility 20 of the system 100.

In accordance with the two types of input data PD % and T1% used as an example, an input layer 21 of the conditional generative artificial neural network 22 is provided with five nodes. Two nodes (i.e., the first two nodes from the top in FIG. 2) of the input layer 21 are input nodes for PD % and T1%, and three nodes (i.e., the last three nodes from the top in FIG. 2) of the input layer 21 are input nodes for the entries $c_i$ of the condition vector c.

As described herein, the first entry c1 can indicate a percentage of a T1-weighting, the second entry c2 a percentage of a T2-weighting, and the third entry c3 a percentage of a PD-weighting and hence condition, i.e. influence, the conditional generative artificial neural network 22 accordingly in order to generate setting parameters 70 according to the percentages indicated by the condition vector c.

In an embodiment, if the conditional generative artificial neural network 22 is to specify further conditions as the weighting percentages, the condition vector c can accordingly receive further entries, wherein the input layer 21 for each further entry of the condition vector c is equipped with a further input node. For example, a "1" in a fourth entry of the condition vector c could mean that an MRI sequence is to be performed on a human head, a "1" in a fifth entry of the condition vector c could mean that an MRI sequence is to be performed on a human heart, a "1" in a sixth entry of the condition vector c could mean that an MRI sequence is to be carried out on an unspecified body part, a value in a seventh entry of the condition vector c could indicate a body-fat percentage of a body on which the MRI sequence is to be performed, etc.

In an embodiment, the nodes of the input layer 21 are fully connected via trainable weights $W_h$ with nodes in a hidden layer 23 of the conditional generative artificial neural network 22, i.e. the hidden layer 23 is a fully-connected layer. The nodes in the hidden layer 23 have a respective bias $b_h$ as a trainable parameter and an activation unit, for example a sigmoid unit, as indicated in FIG. 2, a tan h-activation unit, etc.

Again, the hidden layer 23 advantageously may be comprised of any suitable number of nodes (e.g., more than five nodes, more than ten nodes, more than twenty nodes, more than forty nodes, more than forty-eight nodes, etc.). Tests have found that forty-eight nodes strikes a good balance between accuracy and computational effort.

The hidden layer 23 is advantageously fully connected to an output layer 25, which is hence also implemented as a fully connected layer. For the connections between the nodes of the hidden layer 23 and the nodes of the output layer 25, the output layer 25 has weights $W_s$ as trainable parameters.

The output layer 25 advantageously may include one node for each setting parameter 70 to be generated. Hence, if only the echo time TE and the repetition time TR are generated, the output layer 25 advantageously may include two nodes. The nodes each have a bias $b_s$ as a trainable parameter and an activation function (e.g., a linear activation function, as indicated in FIG. 2).

In an embodiment, it is also possible to use other types of input data instead of or in addition to the named input data 80. For example, this may include a complete MRI protocol or an MRI sequence, together with a condition (e.g., a magnetic field strength, a body part to be examined, or one of the other aforementioned conditions). The conditional generative artificial neural network 22 can be implemented to generate correspondingly conditioned setting parameters 70 from this input data 80 (e.g., an MRI protocol or MRI sequence adapted to the magnetic field strength specified in the condition).

FIG. 3 illustrates a schematic flow diagram to explain a method for establishing a system for generating setting parameters for an MRI sequence to be performed in accordance with an embodiment of the disclosure. FIG. 3 shows a schematic flow diagram to explain a method for establishing a system for generating setting parameters for an MRI sequence to be performed in accordance with an embodiment of the disclosure. The flow diagram shown in FIG. 3 may establish a system in accordance with an embodiment of the present disclosure. The flow in accordance with FIG. 3 may be suitable for establishing the system 100 as shown and described in accordance with FIG. 1 and can be adapted in accordance with all the embodiments, options, variants, and developments described with respect to the system 100, and vice versa. The flow in accordance with FIG. 3 is partially described using the reference characters in FIG. 1 and FIG. 2 by way of example and not limitation, and the flow shown in FIG. 3 is not mandatorily restricted to the system 100 as shown and described with reference to FIGS. 1 and 2.

The method may begin when training data is generated (e.g., calculated, loaded, retrieved, etc.) (block S10) comprising input data 80 relating to the MRI sequence to be performed and comprising corresponding setting parameters 70 as labels.

The method may include generating (e.g., calculating, loading, retrieving, etc.) (block S20) a conditional generative artificial neural network 22 and a conditional discriminative artificial neural network. The conditional generative artificial neural network 22 may be, for instance, the same as that described above and elsewhere herein. For example, the conditional discriminative artificial neural network may advantageously comprise an input layer with a number of nodes corresponding to the sum of the generated setting parameters 70 and the entries of the condition vector c, i.e. as shown in the example in FIG. 2 having five nodes, for example.

The conditional discriminative artificial neural network further comprises a hidden layer that may be comprised of any suitable number of nodes (e.g., more than five nodes, more than ten nodes, more than twenty nodes, more than forty nodes, between thirty and sixty nodes, between forty and fifty nodes, more than or equal to forty-eight nodes, etc.). In an embodiment, one output layer of the conditional discriminative artificial neural network comprises one individual output node of which the output indicates whether the conditional discriminative artificial neural network classifies an input vector as "true" (i.e. belonging to the training data) or "false" (i.e. generated by the conditional generative artificial neural network 22), for example by "0" for "true" and "1" for "false."

The method may include training (block S30) the conditional generative artificial neural network 22 using the training data provided in order to generate the setting parameters 70 for MRI sequences to be performed based on the input data 80 of the training data. As an example, the conditional generative artificial neural network may be conditional in order to generate setting parameters for in each case at least one T1-weighted MRI sequence, one T2-weighted MRI sequence, and one proton-density-weighted MRI sequence. During the training (block S30), the conditional generative artificial neural network may advantageously also be conditioned, for example uniformly, by each of the possible conditions, i.e. subjected to each of the possible conditions to the same extent as far as possible.

The method may include training (block S40) the conditional discriminative artificial neural network using the training data provided and the setting parameters 70 generated by the conditional generative artificial neural network 22, wherein the conditional discriminative artificial neural network is trained in order to discriminate, for each individual parameter set, whether this belongs to the training data or to the setting parameters generated by the conditional generative artificial neural network.

The training (block S40) may include training the conditional generative artificial neural network 22 to generate the setting parameters 70 such that the conditional discriminative artificial neural network is not able to discriminate the setting parameters of the training data from the setting parameters 70 generated by the conditional generative artificial neural network 22.

In other words, the conditional generative artificial neural network 22 may be trained as the generative part of a conditional generative adversarial neural net, wherein, for example, the variants of (conditional) generative adversarial neural nets known from the Mirza or Mao references (or also from other sources) can be used.

The method may include receiving (block S50), via an input interface 10, input data 80 relating to MRI sequences to be performed is provided and configured.

The method may include providing and configuring a computing facility 20 to implement the trained conditional generative artificial neural network 22 to generate (block S60) the setting parameters 70 for the MRI sequence to be performed based on the received input data 80.

Figure 4:
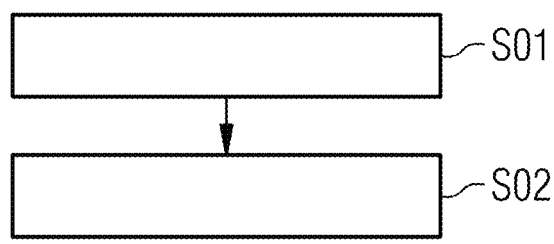
FIG. 4 illustrates a schematic flow diagram to explain a method for generating setting parameters for an MRI sequence to be performed in accordance with an embodiment of the disclosure.

FIG. 4 illustrates a schematic flow diagram to explain a method for generating setting parameters for an MRI sequence to be performed in accordance with an embodiment of the disclosure. The method in accordance with FIG. 4 can be performed, for example, using the system in accordance with an embodiment of the present disclosure and can, therefore, be adapted in accordance with all the modifications, variants, options and developments described in respect of the system in accordance with the system 100 as shown and described with reference to FIG. 1, and vice versa.

The method as shown in FIG. 4 may begin then input data 80 relating to an MRI sequence to be performed is received (block S01), for example as explained above with respect to the input interface 10 and/or the input data 80.

The method may include setting parameters 70 for the MRI sequence to be performed being generated (block S02) using a trained conditional generative artificial neural network 22 based on the received input data 80. This may include, for instance, generating the setting parameters using the trained conditional generative artificial neural network 22 as described above with respect to FIG. 2. The conditional generative artificial neural network 22 is conditional in order to generate setting parameters 70 of, for example, at least one T1-weighted MRI sequence, one T2-weighted MRI sequence, and one proton-density-weighted MRI sequence.

The following discloses examples program code snippets to explain possible variants of the conditional generative artificial neural network 22 and/or the conditional generative adversarial net and demonstrate the effectiveness of the present disclosure.

The program code snippets are written in Google® TensorFlow® Version 1.4.0 by way of example and not limitation. The conditional generative artificial neural network 22 may be implemented in other suitable programming languages.

For purposes of simplicity, the code snippets are divided into input blocks, which are introduced by "In [x]," where "x" stands for a number of respective input blocks. Further comments are inserted for ease of understanding, but the code is otherwise self-explanatory.

```
In [1]:
import numpy as np
import matplotlib.pyplot as plt
% matplotlib inline
In [2]:
import tensorflow as tf
print ("TensorFlow r", tf._version_)
TensorFlow r 1.4.0
#This indicates the version of TensorFlow to be used
```

Advantageous parameter value sets for setting parameters 70, and training data for demonstrating the efficiency of the present disclosure can, for example, be defined and generated in the following way:

```
In [3]:
def ParameterWeightingIdx (TR, TE, T1=1084, T2=69):
# Weighting factors N, T1, T2, N:
SN=1.0
ST1=np.abs (1.0/(1.0−np.exp (TR/T1)))
ST2=np.abs (TE/T2)
# Weighting indices (Total:=1.0)
NWI=SN/(ST+ST2+1.0) # PD-weighting
T1WI=ST1*NWI # T1-weighting
T2WI=ST2*NWI # T2-weighting
return np.vstack ([T1WI, T2WI, NWI]).T
```

Herein, the "weighting indices" NWI, T1WI and T2WI each represent the percentages PD %, T1% and T2% as a decimal fraction, i.e.:

NWI=PD %/100, T1WI=T1%/100, and T2WI=T2%/100.

```
In [4]:
N=600
# T1w
X1=np.dot (np.random.rayleigh (1.0, [N, 2]), [[120., 8.]])+[600., 10.]
C1=np.tile (np.eye (3) [0], N). reshape ((N, 3)) # [1. 0. 0.]
# C1=ParameterWeightingIdx(X1[:, 1])
# T2w
X2=np.dot (np.random.rayleigh (2.0, [N, 2]), [[−100., 0.], [0., −6.]])+[3000., 120.]
C2=np.tile (np.eye (3)[1], N). reshape ((N,3)) # [0. 1. 0.]
# C2=ParameterWeightingIdx(X2[:, 1])
# PDw
X3=np.dot (np.random.rayleigh (2.0, [N, 2]), [[−100.], [−30., 6.]])+[3000., 10.]
C3=np.tile (np.eye (3)[2], N). reshape ((N,3)) # [0. 0. 1.]
X=np.concatenate ([X1, X2, X3]) # Value
C=np.concatenate ([C1, C2, C3]) # Label
In [5]:
train_data=np.concatenate ([X, C], 1)
T1mask=(np.logical_and(train_data[::,2]>train_data[::,3], train_data[::, 2]>train
  _data[::,4]))
T2mask=(np.logical_and(train_data[::,3]>train_data[::,2], train_data[::3,]>train
  _data[::,4]))
PDmask=(np.logical_and(train_data[::,4]>train_data[::,2], train_data[::,4]>train
  _data[::,3]))
print (T1mask)
[True True True . . . , False False False]
```

In practice, the training data is not randomly generated with np.random.rayleigh, but rather taken from datasets with known setting parameters 70.

The following code structure can be used, for example, to generate the conditional generative adversarial net, for example:

In [8]:
```
def sampleZ(Ncol):
    return np.random.uniform(-1.0, 1.0, size=(Ncol,2)) # np.random.randn(Ncol,2)
def netG(z, c, reuse=False):
    with tf.variable_scope('generator', reuse=reuse):
        z_conditioned=tf.concat([z, c], 1)
        G_input=tf.contrib.layers.fully_connected(z_conditioned, 48, activation_fn=tf.nn.tanh)
        G_output=tf.contrib.layers._(G_input, 2, activation_fn=None)
        return G_output
def netD(x,c, reuse=False):
    with tf.variable_scope('discriminator', reuse=reuse):
        x_conditioned=tf.concat([x, c], 1)
        D_input=tf.contrib.layers.fully_connected(x_conditioned, 48, activation_fn=tf.nn.tan h)
        D_output=tf.contrib.layers.fully_connected(D_input, 1, activation_fn=tf.nn.tan h)
        return D_output
```
In [9]:
```
z=tf.placeholder(tf.float32, shape=[None, 2], name='G_input')
x=tf.placeholder(tf.float32, shape=[None, 2], name='D_input')
c=tf.placeholder(tf.float32, shape=[None, 3], name='C label')
G_sample=netG(z, c)
D_real=netD(x, c)
D_fake=netD(G_sample, c, reuse=True)
D_var=tf.trainable_variables(scope='discriminator')
G_var=tf.trainable_variables(scope='generator')
```

Furthermore, a loss function (also "cost function") D_loss is defined for the conditional discriminative artificial neural network, and a loss function G_loss is defined for the conditional generative artificial neural network 22 and used in the training (blocks S30, S40) of the conditional generative adversarial net (i.e. the generative part thereof and the discriminative part thereof) in the context of backpropagation.

Such loss functions D_loss and G_loss may be implemented, for instance, as loss functions according to the least squares method see (see also Mao), for example as shown in the following code snippet:

In [10]:
```
# generative adversarial net with least squares loss function ("Least-Squares GAN")
D_loss=0.5*tf.reduce_mean(tf.square(D_real+0.5*tf.reduce_mean(tf.square(D_fake))
G_loss=0.5*tf.reduce_mean(tf.square(D_fake-1))
G_solver=tf.train.AdamOptimizer(learning_rate=1.e-5).minimize(G_loss, var_list=G_var, name='G_solver')
D_solver=tf.train.AdamOptimizer(learning_rate=5.e-5).minimize(D_loss, var_list=D_var, name='D_solver')
```

"TensorBoard" can be used to generate and process a graphical representation, for example, as shown in the following code snippet:

In [11]:
```
tf.summary.histogram('D_real', D_real)
tf.summary.histogram(D_'fake', D_fake)
tf.summary.scalar('D_loss', D_loss)
tf.summary.scalar('G_loss', G_loss)
[tf.summary.histogram(ii.name.replace(':', '_'), ii) for ii in G_var]
[tf.summary.histogram(jj.name.replace(':', '_'), jj) for jj in D_var]
```
Out [11]:
```
[<tf.Tensor 'discriminator/fully_connected/weights_0:0' shape=( ) dtype=string>,
 tf.Tensor 'discriminator/fully_connected/biases_0:0' shape=( ) dtype=string>,
 tf.Tensor 'discriminator/fully_connected_1/weights_0:0' shape=( ) dtype=string>,
 tf.Tensor 'discriminator/fully_connected_1/biases_0:0' shape=( ) dtype=string>]
```

The training (blocks S30, S40) of the generative adversarial net may be performed, for example, as shown in the following code snippet:

In [12]:
```
PLOT_INLINE=True
```
In [13]:
```
training_size=train_data.shape[0]
batch_size=100
```
In [14]:
```
sess=tf.Session( )
# TensorBoard—tensorboard—logdir=
summary_collection=tf.summary.merge_all( )
tf_writer=tf.summary.FileWriter(".\\tmp\\Image_Weighting_CGAN", sess.graph)
# Initialize
sess.run(tf.global_variables_initializer( ))
```

Subsequently, the results can, for example, be displayed in accordance with the following code snippet:

In[15]:
```
def plot_generated_results(batch_size, label=True, figsize=(10,5)):
    fig, ax=plt.subplots(1,1, figsize=figsize)
    X=np.dot(train_data[:,:2]+0.5, [[3000.], [0., 120.]])
    ax.scatter(X[:, 0],X[:,1], s=0.1)
    C1=np.tile(np.array([1.0, 0.0, 0.0]),batch_size).reshape(batch_size,3)
    C2=np.tile(np.array([0.0, 1.0, 0.0]),batch_size).reshape(batch_size,3)
    C3=np.tile(np.array([0.0, 0.0, 1.0]),batch_size).reshape(batch_size,3)
    T1W=np.asarray(sess.run([G_sample], feed_dict={z: sampleZ(batch_size), c: C1}))
    T1W=np.squeeze(T1W)
    T1W=np.dot(T1W+0.5, [[3000., 0.],[0., 120.]])
    ax.scatter(T1W[:,0],T1W[:,1], s=1.2, c='orange')
    T2W=np.asarray(sess.run([G_sample], feed_dict={z: sampleZ(batch_size), c: C2}))
    T2W=np.squeeze(T2W)
    T2W=np.dot(T2W+0.5, [[3000., 0.],[0., 120.]])
    ax.scatter(T2W[:,0],T2W[:,1], s=1.2, c='green')
    PDW=np.asarray(sess.run([G_sample], feed_dict={z: sampleZ(batch_size), c: C3}))
    PDW=np.squeeze(PDW)
    PDW=np.dot(PDW+0.5, [[3000., 0.],[0., 120.]])
    ax. scatter(PDW[:,0],PDW[:,1], s=1.2, c='red')
    if label:
        fig.suptitle('Generated Data (T1W, T2W, PDW)', fontweight='bold')
        ax.set_xlabel('TR [ms]', fontweight='bold')
        ax.set_ylabel('TE [ms]', fontweight='bold')
        ax.legend(['REF', 'T1W', 'T2W', 'PDW'], markerscale=5., loc='upper left')
    else:
        ax.set_xticks([ ])
        ax.set_yticks([ ])
    plt.show( )
```

Obviously, the code snippets shown can be used in various embodiments, although there is may be any suitable number of alternative possible implementations.

Figure 5:
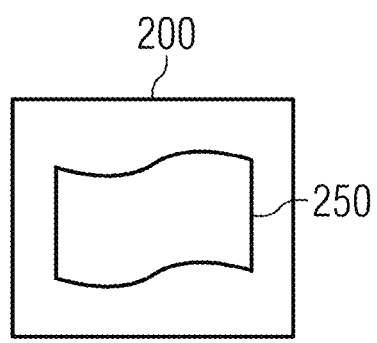
FIG. 5 illustrates a schematic representation of a computer program product in accordance with an embodiment of the disclosure.

FIG. 5 shows a schematic representation of a computer program product 200 in accordance with an embodiment of present disclosure. The computer program product 200 comprises executable program code 250, which is embodied to perform a method in accordance with an embodiment the present disclosure when it is executed. This method may include, for instance, the method as shown and described herein with reference to FIG. 4.

Figure 6:
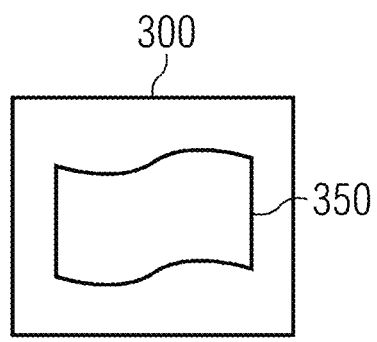
FIG. 6 illustrates a schematic representation of a non-volatile data storage medium in accordance with an embodiment of the disclosure.

FIG. 6 shows a schematic representation of a non-volatile data storage medium 300 in accordance with an embodiment of the present disclosure. The data-storage medium 300 comprises executable program code 350, which may be implemented, for instance, to perform a method in accordance with an embodiment of the present disclosure when it is executed. This method may include, for instance, the method as shown and described herein with reference to FIG. 4.

The program code 250, 350 as shown and described with reference to FIGS. 5 and 6, respectively, may be non-transitory computer-readable media and/or be loaded, stored, accessed, retrieved, etc., via one or more components (e.g., a control computer) accessible to, integrated with, and/or in communication with an MRI scanner device. Although not shown in the Figures for purposes of brevity, the MRI scanner performing the MRI sequences as discussed herein may also include, be integrated with, and/or communicate with the system 100, as shown in FIG. 1. Thus, the various embodiments as described herein may be performed via the operation of an MRI scanner in this manner, which may be facilitated in whole or in part via the execution of program code 250 and/or 350.

Furthermore, any portions of the embodiments described herein may be executed manually, semi-autonomously, or fully autonomously. To provide an illustrative example of the overall operation of the embodiments as described herein, one or more components of or associated with the MRI scanner performing the MRI sequences as discussed herein (e.g., the system 100) may generate one or more control signals (or receive one or more control signals from other portions of the MRI scanner) that result in the execution of various operations. These operations may include, for instance, executing the various methods as disused herein.

Moreover, the various data discussed herein that is used in accordance with generating setting parameters for a MRI sequence to be performed in accordance with an MRI scanner may, once acquired, be stored in any suitable format and in any suitable type of storage medium. For instance, the data may be stored as one or more data files in a memory location that is accessible by the system 100 and/or the MRI scanner as described herein.

In various embodiments, one or more processors associated with the MRI scanner (e.g., the system 100 and/or the control computer as described herein) may likewise generate one or more control signals in response to user input, in response to the execution of computer-readable instructions, and/or upon accessing or reading the acquired and stored data, such as the various types of data described herein (e.g., setting parameters data, MRI sequencing data, etc.). The control signals generated in this manner may thus result in the system 100, the MRI scanner, the control computer associated with the MRI scanner, etc., performing the various methods as described herein. The various computing acts performed by the system 100, the MRI scanner, the control computer associated with the MRI scanner, etc. may be in response to any combination of user input and/or control signals that are automatically generated in response to the occurrence of certain events, e.g., upon the generation of training data, upon the generation of the generate setting parameters, etc.

In the detailed description above, different features have been combined in one or more examples in order to improve the conciseness of the explanation. However, it should be clear that the above description is purely for illustrative purposes, but is in no way limiting. It covers all alternatives, modifications and equivalents of the different features and exemplary embodiments. Many other examples will be immediately and directly clear to the person skilled in the art on reading the above description on account of knowledge in the art.

The exemplary embodiments have been selected and described in to establish possible implementations on which the embodiments as described in the disclosure may be based and the possible applications thereof in practice. As a result, persons skilled in the art can modify and use the different exemplary embodiments thereof with regard to a particular application or intended use.

Again, the embodiments of the methods and apparatuses described herein are by way of example and not limitation. The various embodiments described herein may be further modified by a person skilled in the art without departing from the spirit and scope of the disclosure. Furthermore, although the present disclosure has been illustrated and described in detail with the preferred exemplary embodiments, the disclosure is not restricted by the examples given, and other variations can be derived therefrom by a person skilled in the art without departing from the protective scope of the disclosure. Although modifications and changes may be suggested by those skilled in the art, it is the intention of the inventors to embody within the patent warranted hereon all changes and modifications as reasonably and properly come within the scope of their contribution to the art.

It is also pointed out for the sake of completeness that the use of the indefinite articles "a" or "an" does not exclude the possibility that the features in question may also be present more than once. Similarly, the term "unit" does not rule out the possibility that the same consists of a plurality of components which, where necessary, may also be distributed in space.

The claims described herein and the following description in each case contain additional advantages and developments of the embodiments as described herein. In various embodiments, the claims of one claims category can, at the same time, be developed analogously to the claims of a different claims category and the parts of the description pertaining thereto. Furthermore, the various features of different exemplary embodiments and claims may also be combined to create new exemplary embodiments without departing from the spirit and scope of the disclosure.

REFERENCES

The following references are cited throughout this disclosure as applicable to provide additional clarity, particularly with regards to terminology. These citations are made by way of example and ease of explanation and not by way of limitation.

Citations to the following references are made throughout the application using a matching bracketed number, e.g., [1].

[1] R. W. Brown et al.: "Magnetic Resonance Imaging: Physical Principles and Sequence Design," Wiley-Blackwell, 2nd edition (Jun. 23, 2014), ISBN-13: 978-0471720850.
[2] I. J. Goodfellow et al.: "Generative Adversarial Nets," in: Advances in Neural Information Processing system 27 (NIPS 2014), edited by Z. Ghahramani et al., URL: https://papers.nips.cc/paper/5423-generative-adversarial-nets.
[3] Mirza et al.: "Conditional Generative Adversarial Nets," arXiv preprint arXiv:1411.1784v1, submitted on Nov. 6, 2014, URL: https://arxiv.org/abs/1411.1784. Hereinafter, this publication is cited as "Mirza et al."
[4] X. Mao et al.: "Least Squares Generative Adversarial Networks," arXiv preprint arXiv:1611.04076v3, submitted on Nov. 13, 2016, last revised on Apr. 5, 2017, URL: https://arxiv.org/abs/1611.04076. Hereinafter, this publication is be cited as "Mao et al."

What is claimed is:

1. A system for generating setting parameters for a magnetic resonance imaging (MRI) sequence to be performed in accordance with an MRI scanner, comprising:
   an input interface configured to receive input data having a data structure corresponding to an input vector indicating a percentage of one or more types of MRI sequences to be performed; and
   a conditional generative artificial neural network configured to be trained as part of a conditional generative adversarial net to generate setting parameters for the MRI sequence to be performed based on the input data received from the input interface relating to the MRI sequence, the conditional generative adversarial net comprising the conditional generative artificial neural network as a generative part and a conditional discriminative artificial neural network as a discriminative part,
   wherein the conditional generative artificial neural network is provided with conditions to be fulfilled with respect to the percentage of the one or more types of MRI sequences to be performed so as to generate setting parameters for one T1-weighted MRI sequence, one T2-weighted MRI sequence, and one proton-density-weighted (PD-weighted) MRI sequence,
   wherein the conditions to be fulfilled are provided to the conditional generative artificial neural network as a concatenation of a condition vector with the input vector, and
   wherein the condition vector has a data structure comprising non-zero entries that respectively indicate a percentage of the one or more types of MRI sequences to be performed.

2. The system as claimed in claim 1, wherein the input data comprises or indicates at least one of the following percentages:
   a percentage with which the MRI sequence to be performed is to be T1-weighted,
   a percentage with which the MRI sequence to be performed is to be T2-weighted, and
   a percentage with which the MRI sequence to be performed is to be PD-weighted.

3. The system of claim 2, wherein the input data includes a plurality of input vectors, each respective one of the plurality of input vectors having respective entries corresponding to (i) a percentage with which the MRI sequence to be performed is to be T1-weighted, (ii) a percentage with which the MRI sequence to be performed is to be T2-weighted, and (iii) a percentage with which the MRI sequence to be performed is to be PD-weighted.

4. The system of claim 3, wherein the conditional generative artificial neural network is provided with the conditions to be fulfilled by concatenating a respective one of a plurality of condition vectors with a respective one of the plurality of input vectors.

5. The system of claim 4, wherein the plurality of condition vectors each have respective entries identifying which one of the T1-weighted MRI sequence, the T2-weighted MRI sequence, or the PD-weighted MRI sequence that an entry of a respectively concatenated one of the plurality of input vectors corresponds.

6. The system as claimed in claim 1,
   wherein the setting parameters comprise a repetition time and an echo time for the MRI sequence to be performed.

7. The system as claimed in claim 1,
   wherein the setting parameters comprise a turbo factor and/or a bandwidth for the MRI sequence to be performed.

8. The system as claimed in claim 1,
   wherein the conditional generative artificial neural network is additionally provided with conditions to be fulfilled with respect to at least one of the following conditions:
      a magnetic field strength for the MRI sequence to be performed,
      information regarding a location and/or an alignment of a sectional plane through a body on which the MRI sequence is to be performed,
      information regarding a location and/or a body part of a body on which the MRI sequence is to be performed,
      a body-fat percentage, and
      artifact suppression.

9. The system as claimed in claim 1, wherein the conditional generative artificial neural network comprises an input layer, an output layer, and an intermediate hidden layer.

10. The system as claimed in claim 9, wherein the conditional generative artificial neural network further comprises at least one hidden layer, and
    wherein the input layer and the at least one hidden layer form at least one part of an autoencoder network.

11. The system as claimed in claim 1, wherein the conditional generative artificial neural network includes a multilayer perceptron.

12. A computer-implemented method for establishing a system for generating setting parameters for a magnetic resonance imaging (MRI) sequence to be performed in accordance with an MRI scanner, the method comprising:
    operating an MRI scanner to generate training data comprising input data relating to the MRI sequence to be performed, the input data having a data structure corresponding to an input vector including corresponding setting parameters as labels and indicating a percentage of one or more types of MRI sequences to be performed;
    operating the MRI scanner to generate a conditional generative artificial neural network and a conditional discriminative artificial neural network;
    operating the MRI scanner to train the conditional generative artificial neural network using the training data, the conditional generative artificial neural network being trained such that the setting parameters for MRI sequences to be performed are generated based on the input data, the conditional generative artificial neural network being provided with conditions to be fulfilled with respect to the percentage of the one or more types of MRI sequences to be performed such that setting parameters are generated for, respectively, at least one T1-weighted MRI sequence, one T2-weighted MRI sequence, and one proton-density-weighted MRI sequence, wherein the conditions to be fulfilled are provided to the conditional generative artificial neural network as a concatenation of a condition vector with the input vector, and wherein the condition vector has a data structure comprising non-zero entries that respectively indicate a percentage of the one or more types of MRI sequences to be performed;

operating the MRI scanner to train the conditional discriminative artificial neural network using the training data and the setting parameters generated by the conditional generative artificial neural network, the trained conditional discriminative artificial neural network being configured to discriminate, for each respective one of the setting parameters from among the generated setting parameters, whether each setting parameter is associated with the training data or is associated with the setting parameters generated by the conditional generative artificial neural network, the conditional generative artificial neural network being further trained until the conditional discriminative artificial neural network is unable to discriminate the training data from the setting parameters generated by the conditional generative artificial neural network; and operating the MRI scanner to perform MRI sequences in accordance with the received input data and the setting parameters generated using the trained conditional generative artificial neural network.

13. The method as claimed in claim 12, wherein the training of the conditional generative artificial neural network and/or the training of the conditional discriminative artificial neural network is performed using a loss function based on the least squares method.

14. A computer-implemented method for establishing a system for generating setting parameters for a magnetic resonance imaging (MRI) sequence to be performed in accordance with an MRI scanner, the method comprising:

operating an MRI scanner to receive input data in the form of a data structure corresponding to an input vector indicating a percentage of one or more types of MRI sequences to be performed; and operating an MRI scanner to generate, using a conditional generative artificial neural network that has been trained as part of a conditional generative adversarial net, setting parameters for the MRI sequence to be performed based on the received input data, wherein the conditional generative adversarial net comprises the conditional generative artificial neural network as a generative part and a conditional discriminative artificial neural network as a discriminative part; and wherein the conditional generative artificial neural network is provided with conditions to be fulfilled with respect to the percentage of the one or more types of MRI sequences to be performed such that setting parameters are generated for, respectively, at least one T1-weighted MRI sequence, one T2-weighted MRI sequence, and one proton-density-weighted MRI sequence, wherein the conditions to be fulfilled are provided to the conditional generative artificial neural network as a concatenation of a condition vector with the input vector, and wherein the condition vector has a data structure comprising non-zero entries that respectively indicate a percentage of the one or more types of MRI sequences to be performed.

15. The method as claimed in claim 14, wherein the setting parameters comprise a repetition time, an echo time, a turbo factor and/or a bandwidth for the MRI sequence to be performed.

16. The method as claimed in claim 14, wherein the conditional generative artificial neural network is additionally provided with conditions to be fulfilled with respect to:

a magnetic field strength for the MRI sequence to be performed, information regarding a location and/or an alignment of a sectional plane through a body on which the MRI sequence is to be performed, information regarding a location and/or a body part of a body on which the MRI sequence is to be performed, a body-fat percentage, and an artifact suppression.

17. A non-transitory computer readable medium loaded onto a control computer of a magnetic resonance imaging (MRI) scanner for generating setting parameters for a magnetic resonance imaging (MRI) sequence to be performed, the non-transitory computer readable medium having instructions stored thereon that, when executed by the control computer, cause the MRI scanner to:

receive input data in the form of a data structure corresponding to an input vector indicating a percentage of one or more types of MRI sequences to be performed; and generate, using a trained conditional generative artificial neural network that has been trained as part of a conditional generative adversarial net, setting parameters for the MRI sequence to be performed based on the received input data, wherein the conditional generative adversarial net comprises the conditional generative artificial neural network as a generative part and a conditional discriminative artificial neural network as a discriminative part; and wherein the conditional generative artificial neural network is provided with conditions to be fulfilled with respect to the percentage of the one or more types of MRI sequences to be performed such that setting parameters are generated for, respectively, at least one T1-weighted MRI sequence, one T2-weighted MRI sequence, and one proton-density-weighted MRI sequence, wherein the conditions to be fulfilled are provided to the conditional generative artificial neural network as a concatenation of a condition vector with the input vector, and wherein the condition vector has a data structure comprising non-zero entries that respectively indicate a percentage of the one or more types of MRI sequences to be performed.

18. The non-transitory computer readable medium as claimed in claim 17, wherein the setting parameters comprise a repetition time, an echo time, a turbo factor and/or a bandwidth for the MRI sequence to be performed.

19. The non-transitory computer readable medium as claimed in claim 17, wherein the conditional generative artificial neural network is additionally conditioned by at least one of the following conditions:
- a magnetic field strength for the MRI sequence to be performed,
- information regarding a location and/or an alignment of a sectional plane through a body on which the MRI sequence is to be performed,
- information regarding a location and/or a body part of a body on which the MRI sequence is to be performed,
- a body-fat percentage, and
- an artifact suppression.

* * * * *